US012805860B2

(12) United States Patent
Tong et al.

(10) Patent No.: US 12,805,860 B2
(45) Date of Patent: Nov. 24, 2026

(54) TISSUE SUTURING DEVICE

(71) Applicant: Cilag GmbH International, Zug (CH)

(72) Inventors: Weiwen Tong, Shanghai (CN); Xingyan Lu, Shanghai (CN); Qinglong Liu, Shanghai (CN); Jie Tang, Shanghai (CN); Xiang Wan, Shanghai (CN)

(73) Assignee: Cilag GmbH International, Zug (CH)

( * ) Notice: Subject to any disclaimer, the term of this patent is extended or adjusted under 35 U.S.C. 154(b) by 238 days.

(21) Appl. No.: 18/719,899

(22) PCT Filed: Dec. 14, 2022

(86) PCT No.: PCT/IB2022/062208
§ 371 (c)(1),
(2) Date: Jun. 14, 2024

(87) PCT Pub. No.: WO2023/111890
PCT Pub. Date: Jun. 22, 2023

(65) Prior Publication Data
US 2025/0049431 A1 Feb. 13, 2025

(30) Foreign Application Priority Data
Dec. 17, 2021 (CN) ......................... 202111552006.6

(51) Int. Cl.
*A61B 17/04* (2006.01)
*A61B 17/06* (2006.01)

(52) U.S. Cl.
CPC ...... *A61B 17/0469* (2013.01); *A61B 17/0482* (2013.01); *A61B 17/06004* (2013.01); *A61B 2017/047* (2013.01)

(58) Field of Classification Search
CPC ............ A61B 17/0469; A61B 17/0482; A61B 17/06066; A61B 17/0057; A61B 17/3417;
(Continued)

(56) References Cited

U.S. PATENT DOCUMENTS 5,439,469 A 8/1995 Heaven et al.
5,817,110 A * 10/1998 Kronner ............. A61B 17/0469 606/147

(Continued)

FOREIGN PATENT DOCUMENTS

CN 110279446 A 9/2019

OTHER PUBLICATIONS

International Search Report and Written Opinion dated Feb. 27, 2023, for International Application No. PCT/IB2022/062208, 10 pages.

*Primary Examiner* — Sarah A Long
(74) *Attorney, Agent, or Firm* — FBT Gibbons LLP

(57) ABSTRACT

A tissue suturing device includes a body and a plurality of suture needles. The body includes a guide segment and a tube segment. The guide segment contains a suture needle channel. The tube segment has an accommodating cavity communicated with the suture needle channel. Each of the suture needles includes a main needle segment and a puncture needle segment connected with and spaced apart from the main needle segment. Two of the suture needles, together, connect a suture thread releasably between the puncture needle segments of the two suture needles. The main needle segments are arranged in the suture needle channel. The puncture needle segments carry the suture thread and are located in the accommodating cavity. Each of the suture needles moves along the suture needle channel such that the puncture needle segment returns to the accommodating cavity alone after passing with the suture thread through a tissue wall.

20 Claims, 11 Drawing Sheets

(58) Field of Classification Search

CPC ...... A61B 2017/047; A61B 2017/0608; A61B 2017/00637; A61B 2017/00663; A61B 2090/0062; A61B 90/06; A61B 90/08

See application file for complete search history.

(56) References Cited

U.S. PATENT DOCUMENTS

| | | | | |
|---|---|---|---|---|
| 10,966,707 | B2 * | 4/2021 | Kumar | A61B 17/06066 |
| 2003/0171764 | A1 * | 9/2003 | Debbas | A61B 17/0057<br>606/222 |
| 2018/0221015 | A1 * | 8/2018 | Bhalla | A61B 17/06066 |
| 2020/0214694 | A1 * | 7/2020 | Nobles | A61B 17/0482 |

* cited by examiner

TISSUE SUTURING DEVICE

TECHNICAL FIELD

The present invention relates to the technical field of surgical instruments, and particularly to a tissue suturing device.

BACKGROUND OF THE INVENTION

During surgery, surgeons usually need to use a tissue closure instrument to suture a wound to be sutured, such as an incision in the abdominal cavity of a patient.

Existing tissue closure instruments require a puncture needle to pass through a tissue from the outside of the skin into the abdominal cavity when performing suture. In practice, due to differences between individuals, the puncture process of the puncture needle from the outside to the inside may cause injuries to the surrounding organs in the abdominal cavity. Therefore, experienced surgeons are usually required to perform the puncture.

In addition, the use of the existing tissue closure instruments requires the surgeon to hold the tissue closure instrument in one hand and the puncture needle in the other hand for puncture, which is inconvenient to use. In addition, the puncture with one hand may cause shaking, which further causes tissue injuries.

BRIEF SUMMARY

An object of the present invention is to provide a tissue suturing device, which can avoid the risk of injuring other organs around a tissue when the suture needles are puncturing the tissue and improve the safety of the surgical operation.

To achieve the above object, the present invention provides a tissue suturing device comprising: a body, comprising a guide segment at a proximal end for extending into a wound to be sutured in a tissue wall and a tube segment at a distal end, where the guide segment is provided with a suture needle channel, and the tube segment is provided therein with an accommodating cavity communicated with the suture needle channel; a plurality of suture needles, each of which comprising a main needle segment and a puncture needle segment connected with and spaced apart from the main needle segment, where two of the suture needles are used as a group of suture needles to connect a suture thread releasably between the puncture needle segments of the two suture needles, the main needle segments of the plurality of suture needles can be arranged in the suture needle channel, and the puncture needle segments are configured to carry the suture thread and be located in the accommodating cavity; where each of the suture needles can be moved toward the proximal end or the distal end along the suture needle channel such that the puncture needle segment can return to the accommodating cavity alone after passing with the suture thread through the tissue wall.

In this technical solution, the body comprises the guide segment and the tube segment, the guide segment has the suture needle channel, the tube segment has the accommodating cavity communicated with the suture needle channel, each of the suture needles comprises the main needle segment and the puncture needle segment connected with and spaced apart from the main needle segment, the puncture needle segments allow the suture thread to be releasably connected between the puncture needle segments of two suture needles, and the puncture needle segments can also carry the suture thread and be located in the accommodating cavity such that the puncture needle segments can puncture from the inside to the outside (to the proximal end). In this way, during the use, the suture thread can be releasably connected between the puncture needle segments of the two suture needles, and the puncture needle segments and the suture thread are placed together in the accommodating cavity, and then the tube segment is placed in the inner cavity through the wound to be sutured such that the tube segment is allowed to contact the tissue wall around the wound to be sutured. In this way, the puncture needle segment is directly facing the tissue wall around the wound to be sutured. At this moment, the suture needle is pulled outward, and thus the puncture needle segment will puncture outward (e.g., in a vertical or oblique manner) with the suture thread to draw the suture thread outward. Then the suture thread drawn out is grabbed (e.g., the suture thread can be clamped by an instrument, or the puncture needle segment and the suture thread can be passed together through an elastomer mentioned below, and when the puncture needle segment returns alone, the elastomer can grab the suture thread). Subsequently, the suture needle is pushed inward so that the puncture needle segment returns alone to the accommodating cavity to complete suture thread arrangement on one side of the wound to be sutured. The suture thread arrangement on the other side of the wound to be sutured can be completed in the same way. Thus, the tissue suturing device can be removed from the wound to be sutured, and then the wound to be sutured can be closed with the arranged suture thread. Therefore, during the outward and inward movements of the suture needles, the puncture needle segments do not contact other surrounding organs that may exist. Therefore, this tissue suturing device can avoid the risk of injuring other organs around the tissue when the suture needles are puncturing the tissue. In addition, due to the guiding effect of the suture needle channel in the guide segment on the main needle segments, the movements of the suture needles can be made more stable, and the stability of the movements of the puncture needle segments can be improved, so as to reduce the injury to the tissue. In this way, the tissue suturing device effectively improves the safety of the surgical operation.

Further, the body comprises a connecting piece, and the guide segment is connected with the tube segment through the connecting piece to form an avoidance space at a tube opening edge of the tube segment.

Further, each of the suture needles comprises a U-shaped needle, the main needle segment and the U-shaped needle are connected, and at least one side needle segment of the U-shaped needle is used as the puncture needle segment.

Furthermore, one side needle segment of the U-shaped needle is connected with the main needle segment, and the other side needle segment of the U-shaped needle is used as the puncture needle segment.

Further, the accommodating cavity is provided therein with a partition board which divides the accommodating cavity into a plurality of chambers, and the puncture needle segment of each of the suture needles can be located in the respective corresponding chamber.

Furthermore, the partition board is provided thereon with a suture thread pre-positioning slot.

Further, the suture needle channel is provided therein with a partition board which divides the suture needle channel into a plurality of channel holes, and the guide segment of each of the suture needles can be located in the respective corresponding channel hole.

Further, a tube opening edge of the tube segment is tilted and extended downward such that when the body is tilted to one side in the wound to be sutured, the tube opening edge tilted and extended downward can be horizontally arranged to contact the tissue wall on the other side of the wound to be sutured.

Further, the body comprises a suture thread positioning segment between the guide segment and the tube segment, and the suture thread positioning segment can allow the outward-moving puncture needle segment to puncture with the suture thread, and allow the suture thread to detach from the puncture needle segment and remain positioned on the suture thread positioning segment when the puncture needle segment withdraws.

Further, the suture thread positioning segment is provided with an elastomer, and the elastomer can expand when the outward-moving puncture needle segment passes through with the suture thread, and shrink when the puncture needle segment withdraws to allow the suture thread to detach from the puncture needle segment and remain positioned on the elastomer.

Further, the suture thread positioning segment comprises a housing channel in which the elastomer is arranged.

Further, the suture thread positioning segment is provided with a suture needle passing channel, and the main needle segments of the plurality of suture needles can be movably arranged in the suture needle passing channel.

Furthermore, the suture thread positioning segment is formed into a cone, a large-diameter end of the cone is oriented toward the guide segment, a small-diameter end of the cone is oriented toward the tube segment, and an inner channel of the cone is used as the suture needle passing channel.

Moreover, the tissue suturing device comprises a positioning device which is arranged on the guide segment and can be moved along the guide segment to a set position, where the positioning device comprises a positioning contact surface configured to contact an outer surface of a cavity wall tissue to clamp the cavity wall tissue together with the tube segment.

Further, the positioning contact surface and a tube opening edge of the tube segment are parallel to each other, and the tube opening edge is configured to contact the tissue wall.

Further, the positioning device comprises a positioning plate and a sleeve arranged tilted on the positioning plate, the positioning plate comprises the positioning contact surface, and the sleeve is sleeved on the guide segment and a positioning structure is arranged therebetween.

Furthermore, an avoidance opening is formed at an obtuse angle connection position between the positioning plate and the sleeve, and the avoidance opening is configured to accommodate at least a portion of the suture thread positioning segment of the body between the guide segment and the tube segment.

Further, the guide segment is provided thereon with a scale line configured to mark the movement of the positioning device to a predetermined position.

Moreover, the guide segment is provided thereon with a plurality of locking structures that can be unlocked, each of which is configured to lock and unlock the corresponding suture needle.

Moreover, the inner tissue suturing device comprises a suture thread, the suture thread can be connected between the puncture needle segments of two of the suture needles, and the puncture needle segments can carry the suture thread and be located in the accommodating cavity.

BRIEF DESCRIPTION OF DRAWINGS

For the sake of better understanding of the above and other objects, features, advantages and functions of the invention, reference may be made to the preferred embodiments shown in the attached drawings. Identical or similar reference numbers in the drawings refer to identical or similar members. It should be understood by those skilled in the art that the drawings are intended to schematically illustrate the preferred embodiments of the invention and have no limitation on the scope of the invention, and various members are not drawn to scale.

LIST OF REFERENCE NUMBERS

Figure 1:
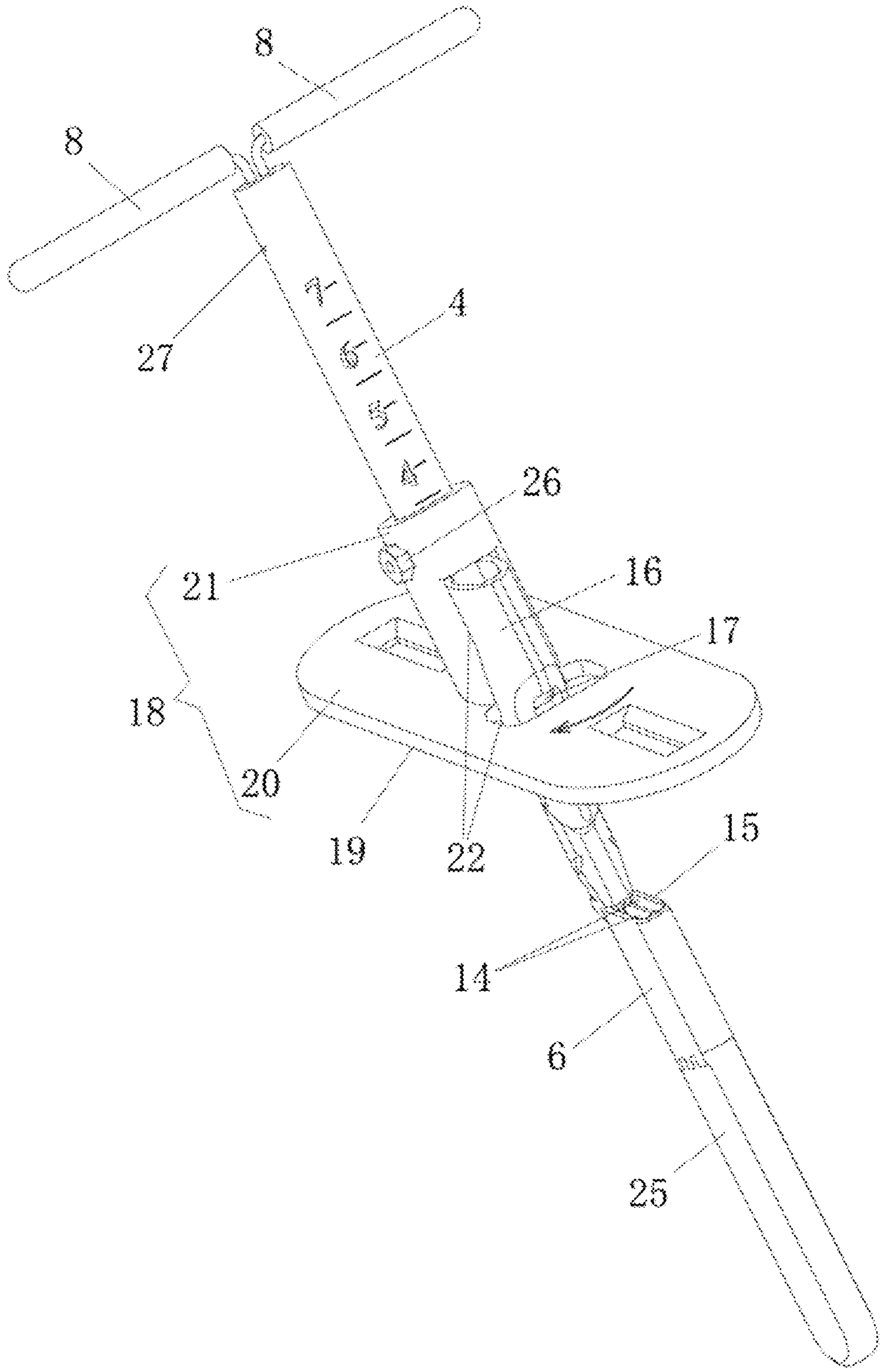
FIG. 1 is a schematic view of a three-dimensional structure of a tissue suturing device provided by a specific embodiment of the invention.

1—Body, 2—cavity wall tissue, 3—wound to be sutured, 4—guide segment, 5—tissue wall, 6—tube segment, 7—accommodating cavity, 8—suture needle, 9—main needle segment, 10—puncture needle segment, 11—connecting piece, 12—U-shaped needle, 13—partition board, 14—chamber, 15—tube opening edge, 16—suture thread positioning segment, 17—housing channel, 18—positioning device, 19—positioning contact surface, 20—positioning plate, 21—sleeve, 22—avoidance opening, 23—scale line, 24—channel hole, 25—extended tube segment, 26—rotary knob, 27—radial hole, 28—inner cavity, 29—suture thread, 30—elastomer, 31—avoidance space.

DETAILED DESCRIPTION

In the detailed description of the embodiments below, explanation is made with reference to the drawings forming part of the description. The drawings show, by way of example, specific embodiments in which the invention is realized. The embodiments shown are not intended to enumerate all embodiments of the present invention. It is understood that other embodiments can be utilized, and that structural or logical changes can be made without departing from the scope of the invention. For the drawings, directional terms such as "lower," "upper," "left," and "right" are used with reference to the orientation of the drawings described. Since components of the embodiments of the invention can be implemented in multiple orientations, these directional terms are used for illustrative rather than restrictive purposes. Therefore, the following specific embodiments are not intended as limitations, and the scope of the invention is defined by the attached claims.

Referring to FIG. 1, FIG. 2, FIG. 3 and FIG. 4, the tissue suturing device provided by the embodiments of the invention comprises a body 1 and a plurality of suture needles 8, where the body 1 comprises a guide segment 4 at a proximal end for extending into a wound to be sutured 3 and a tube segment 6 at a distal end, in which the guide segment 4 is provided with a suture needle channel, and the tube segment 6 is provided therein with an accommodating cavity 7 communicated with the suture needle channel; each of the suture needles 8 comprises a main needle segment 9 and a puncture needle segment 10 connected with and spaced apart from the main needle segment 9, where two of the suture needles are used as a group of suture needles to connect a suture thread releasably between the puncture needle segments 10 of the two suture needles, the main needle segments 9 of the plurality of suture needles 8 can be arranged in the suture needle channel, and the puncture needle segments 10 are configured to carry the suture thread and be located in the accommodating cavity 7; where each of the suture needles 8 can be moved toward the proximal end (outward) or the distal end (inward) along the suture needle channel such that the puncture needle segment 10 can return to the accommodating cavity 7 alone after passing with the suture thread through the tissue wall 5.

In this tissue suturing device, the body 1 comprises the guide segment 4 and the tube segment 6, the guide segment 4 has the suture needle channel, the tube segment 6 is provided with the accommodating cavity 7 communicated with the suture needle channel, each of the suture needles 8 comprises the main needle segment 9 and the puncture needle segment 10 connected with and spaced apart from the main needle segment, the puncture needle segments 10 allow the suture thread to be releasably connected between the puncture needle segments 10 of two suture needles 8, and the puncture needle segments 10 can also carry the suture thread and be located in the accommodating cavity 7 such that the puncture needle segments 10 can puncture from the inside to the outside. In this way, during the use, the suture thread can be releasably connected between the puncture needle segments 10 of the two suture needles, and the puncture needle segments 10 and the suture thread are placed together in the accommodating cavity 7, and then the tube segment 6 is placed in the inner cavity 28 through the wound to be sutured 3 such that the tube segment 6 is allowed to contact the tissue wall 5 around the wound to be sutured. In this way, the puncture needle segment 10 is isolated from other organs that may exist around the wound to be sutured, and the puncture needle segment 10 is directly facing the tissue wall around the wound to be sutured. At this moment, the suture needle 8 is pulled outward, and thus the puncture needle segment 10 will puncture outward (e.g., in an oblique manner) with the suture thread to draw the suture thread outward. Then the suture needle is pushed inward so that the puncture needle segment 10 returns alone to the accommodating cavity 7 to complete suture thread arrangement on one side of the wound to be sutured 3 (referring to FIG. 7). The suture thread arrangement on the other side of the wound to be sutured can be completed in the same way (referring to FIG. 8). Thus, the tissue suturing device can be removed from the wound to be sutured, and then the wound to be sutured can be closed with the arranged suture thread. Therefore, during the outward and inward movements of the suture needles, because the puncture needle segments 10 are accommodated in the accommodating cavity 7, the puncture needle segments 10 do not contact other surrounding organs that may exist. Therefore, this tissue suturing device can avoid the risk of injuring other organs around the tissue when the suture needles are puncturing the tissue. In addition, due to the guiding effect of the suture needle channel in the guide segment on the main needle segments, the movements of the suture needles can be made more stable, and the stability of the movements of the puncture needle segments can be improved, so as to reduce the injury to the tissue. In this way, the tissue suturing device effectively improves the safety of the surgical operation.

In addition, the tissue wall 5 may be a peritoneum of an abdominal cavity or other tissue walls.

In addition, in the tissue suturing device, the guide segment 4 may be connected with the tube segment 6 through a connecting tube. Alternatively, referring to FIG. 2, the body 1 comprises a connecting piece 11, and the guide segment 4 is connected with the tube segment 6 through the connecting piece 11. In this way, an avoidance space 31 can be formed at a tube opening edge 15 of the tube segment 6. When the body 1 is tilted to either side to arrange a suture thread in the wound to be sutured 3, the tissue on one side of the wound to be sutured 3 can be located in the avoidance space, referring to FIG. 7 and FIG. 8, thereby to reduce further compression and injury to the wound to be sutured 3.

In addition, in this tissue suturing device, the suture needle 8 can be of various types, but no matter what type is used, the suture needle 8 only needs to form the puncture needle segment 10 extending from the inside to the outside. For example, in one type, the puncture needle segment 10 can be arranged tilted at a preset angle for puncture relative to the main needle segment 9. For example, the main needle segment 9 and the puncture needle segment 10 form a V-shaped structure. Alternatively, in another type, referring to FIG. 3, FIG. 4 and FIG. 11, each suture needle 8 comprises a U-shaped needle 12, the main needle segment 9 and the U-shaped needle 12 are connected, and at least one side needle segment of the U-shaped needle 12 is used as the puncture needle segment 10. In this way, one or two side needle segments of the U-shaped needle 12 can be used as the puncture needle segment 10. For example, when two side needle segments of a single U-shaped needle 12 are used as the puncture needle segment 10, two suture threads can be arranged at one time on one side of the wound to be sutured 3, which is more favorable for a longer wound to be sutured.

Figure 11:
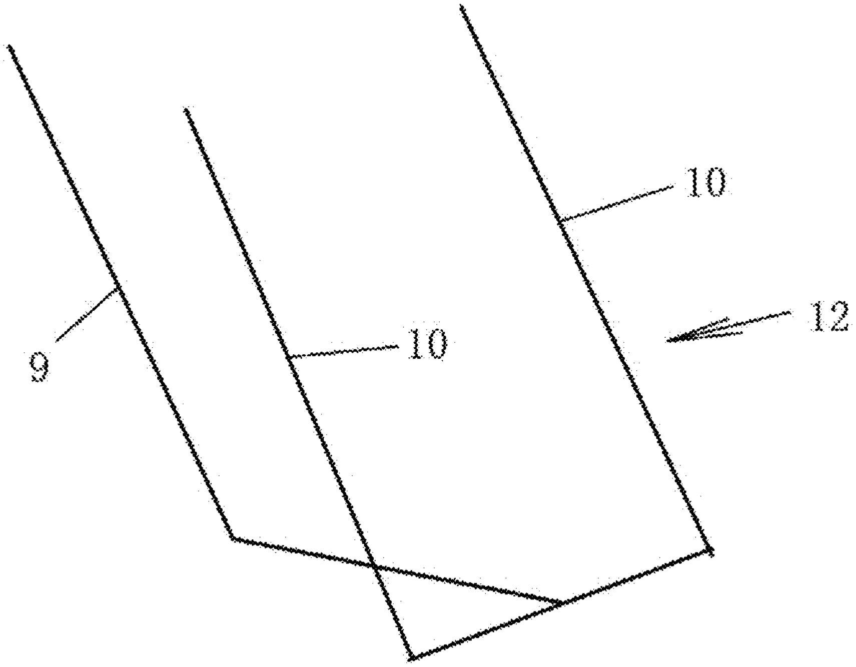
FIG. 11 is a schematic view of a simple structure of another suture needle in a tissue suturing device provided by a specific embodiment of the invention.

Of course, the main needle segment 9 can be connected to a bottom needle segment of the U-shaped needle 12 such that the two side needle segments of the single U-shaped needle 12 serve as the puncture needle segment 10, as shown in FIG. 11. Alternatively, referring to FIG. 3 and FIG. 4, one side needle segment of the U-shaped needle 12 is connected with the main needle segment 9, and the other side needle segment of the U-shaped needle 12 is used as the puncture needle segment 10. Thus, a side needle segment of a single U-shaped needle 12 can complete the arrangement of one suture thread at a time on one side of the wound to be sutured 3.

Additionally, in this tissue suturing device, the accommodating cavity 7 may be a single chamber to allow the puncture needle segments of the plurality of suture needles to be located in the same accommodating cavity 7. Alternatively, referring to FIG. 1, the accommodating cavity 7 is provided therein with a partition board 13 which divides the accommodating cavity 7 into a plurality of chambers 14, and the puncture needle segment 10 of each of the suture needles 8 can be located in the respective corresponding chamber 14. In this way, the puncture needle segments 10 of the plurality of suture needles can be arranged separately to avoid interference among one another.

Additionally, a suture thread pre-positioning slot is formed on the partition board 13. Thus, the suture thread connected between the puncture needle segments 10 can be preset in the suture thread pre-positioning slot to avoid accidental displacement of the suture thread.

In addition, referring to FIG. 1, in the tissue suturing device, the tube segment 6 may be one tube segment or a plurality of tube segments, and the plurality of tube segments may be head-to-tail connected sequentially or may be connected in a manner of integrated molding. For example, one of the plurality of tube segments is an extended tube segment 25 which is connected with the tube segment 6 to extend the distance, thereby making it applicable to puncture needle segments 10 of different lengths. Certainly, the extended tube segment 25 can be flexibly arranged as required. Namely, if the tube segment 6 can accommodate the puncture needle segment 10, it can be connected or not connected with the extended tube segment 25. If the length of the puncture needle segment 10 exceeds that of the tube segment 6, the extended tube segment 25 can be connected to accommodate the long puncture needle segment 10.

Moreover, the suture needle channel may be a single channel, and the main needle segments 9 of the plurality of suture needles may be located in the same suture needle channel. Alternatively, referring to FIG. 2, the suture needle channel is provided therein with a partition board which divides the suture needle channel into a plurality of channel holes 24, and the guide segment 4 of each of the suture needles 8 can be located in the respective corresponding channel hole 24. In this way, the main needle segments 9 of the plurality of suture needles can be arranged separately to avoid interference among one another.

In addition, when the body 1 is arranged vertically, the tube opening edge 15 of the tube segment 6 can be extended horizontally. Alternatively, referring to FIG. 6, the tube opening edge 15 of the tube segment 6 is tilted and extended downward such that when the body 1 is tilted to one side in the wound to be sutured, the tube opening edge 15 tilted and extended downward can be horizontally arranged to contact the tissue wall 5 on the other side of the wound to be sutured, referring to FIG. 7. In this way, the cavity wall tissue 2 can be flatly contacted, making the placement of the tissue suturing device in the wound to be sutured more stable.

Figure 7:
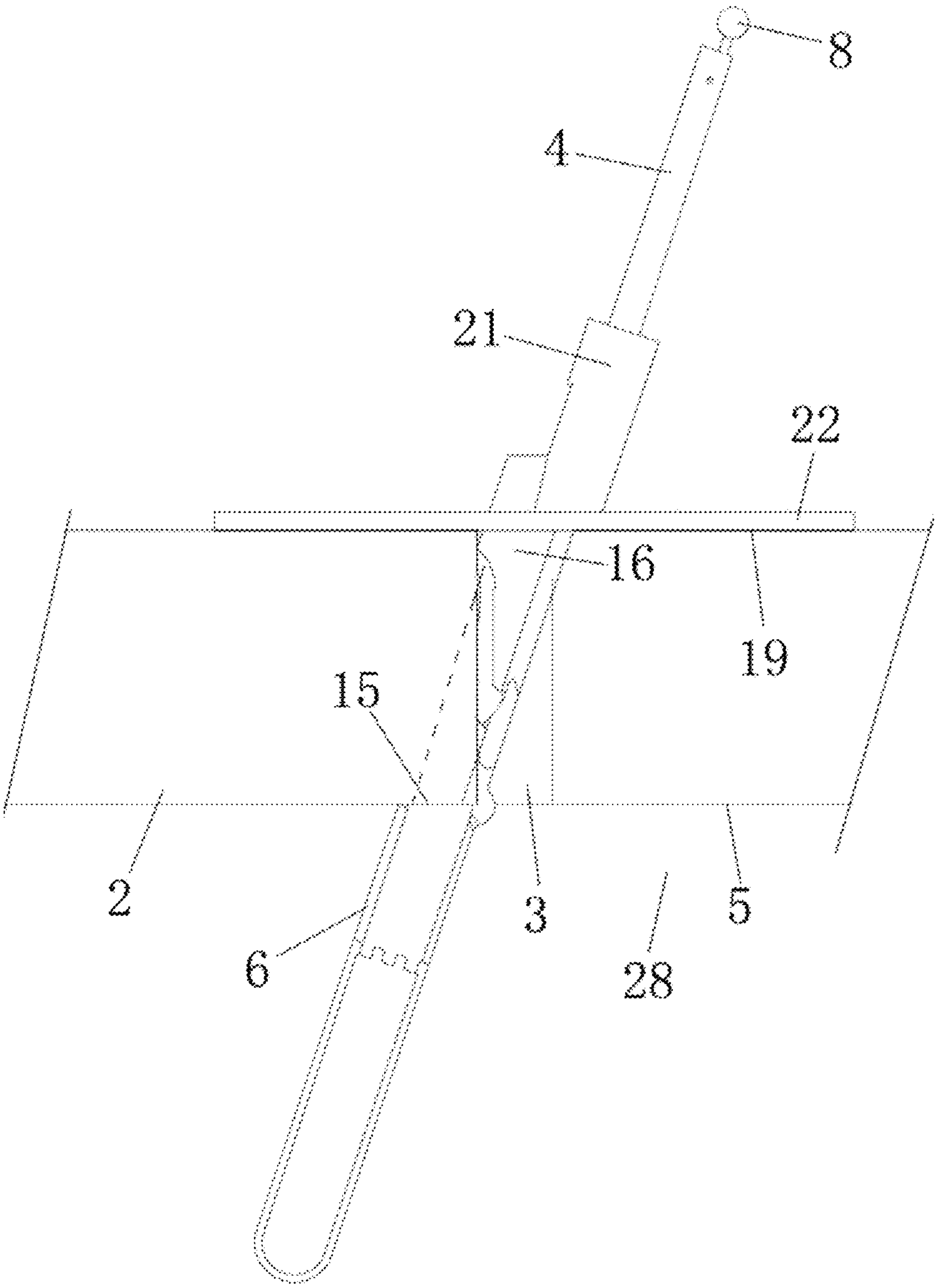
FIG. 7 is a schematic view of the tissue suturing device of FIG. 1 entering a wound to be sutured, and arranging a suture thread on one side, such as the left side, of the wound to be sutured.

In the tissue suturing device, after the puncture needle segment 10 punctures outward and protrudes, the suture thread can be drawn directly to the outside, and an operator can then remove the suture thread from the puncture needle segment 10 so that one sutured thread end is located outside the cavity wall tissue 2. Alternatively, in order to reduce the puncture thickness of the puncture needle segment 10 in the cavity wall tissue 2, for example, during suture of a peritoneum of an abdominal cavity, the puncture needle segment 10 can only pass through the peritoneum. In this way, referring to FIG. 2, the body 1 comprises a suture thread positioning segment 16 located between the guide segment 4 and tube segment 6, and the suture thread positioning segment 16 can allow the outward-moving puncture needle segment 10 to puncture with the suture thread, and allow the suture thread to detach from the puncture needle segment 10 and remain positioned on the suture thread positioning segment 16 when the puncture needle segment 10 that has penetrated therein withdraws. Thus, as shown in FIG. 7, at least part of the suture thread positioning segment 16 can be located in the wound to be sutured 3. In this way, the puncture needle segment 10 enters the suture thread positioning segment 16 after obliquely passing through the tissue of a small thickness. When the puncture needle segment 10 withdraws, the suture thread positioning segment 16 allows the suture thread to detach from the puncture needle segment 10 and remain positioned at the suture thread positioning segment 16. When the tissue suturing device is removed after the suture thread is arranged on both sides, the suture thread positioning segment 16 brings two thread ends of the same suture thread to the outside to facilitate the operator to suture the wound to be sutured.

Of course, the suture thread positioning segment 16 can be of various types. In one type, referring to FIG. 2, the suture thread positioning segment 16 is provided with an elastomer 30. For example, the suture thread positioning segment 16 is provided with an elastomer 30 at the upper end. The elastomer 30 may be silica gel or rubber or other elastic materials. The elastomer 30 can expand when the outward-moving puncture needle segment 10 passes through with the suture thread, and shrink when the puncture needle segment 10 withdraws to allow the suture thread to detach from the puncture needle segment 10 and remain positioned on the elastomer 30. Alternatively, in another type, referring to FIG. 1, the suture thread positioning segment 16 comprises a housing channel 17, which may be one channel or a plurality of channels spaced apart. The housing channel 17 is provided therein with an elastomer 30 so that the puncture needle segment 10 can pass through the elastomer in the housing channel 17. The suture thread positioning segment 16 can be made of other materials, such as rigid plastics, other than the elastomer, such as silica gel.

In addition, in order to guide the suture needle to move stably and reliably, the suture thread positioning segment 16 is provided with a suture needle passing channel, and the main needle segments 9 of a plurality of suture needles 8 can be movably arranged within the suture needle passing channel, which is favorable for a long suture needle.

Additionally, the suture thread positioning segment 16 can be of various shapes. For example, the suture thread positioning segment 16 may be a solid block. Alternatively, referring to FIG. 6, the suture thread positioning segment 16 is formed into a cone, where a large-diameter end of the cone is oriented toward the guide segment 4, a small-diameter end of the cone is oriented toward the tube segment 6, and an inner channel of the cone is used as the suture needle passing channel. In this way, a tapered wall can be conveniently used for passing of the puncture needle segment 10. For example, the housing channel 17 on the tapered wall can facilitate the passing of the puncture needle segment 10.

In addition, in order to improve the convenience of use of the tissue suturing device and avoid the operator from pulling the tissue suturing device in one hand and holding the needle for puncture in the other hand, referring to FIG. 1, the tissue suturing device comprises a positioning device 18 which is arranged on the guide segment 4 and can be moved along the guide segment to locate to the set position. The positioning device 18 comprises a positioning contact surface 19 configured to contact an outer surface of the cavity wall tissue to clamp the cavity wall tissue with the tube segment 6, as shown in FIG. 7. In this way, the positioning device 18 can be adjusted to the set position and allowed to maintain positioned such that the positioning contact surface 19 and the tube segment 16 can clamp the cavity wall tissue together, and thus the tissue suturing device can be clamped stably and reliably on the wound to be sutured. Thus, the operator can operate the suture needle with both hands to perform puncturing and drawing of the suture thread, enabling the operator to operate the suture needle more steadily, avoiding the shaking when the suture needle is operated with one hand, and reducing the injury to the tissue.

Figure 6:
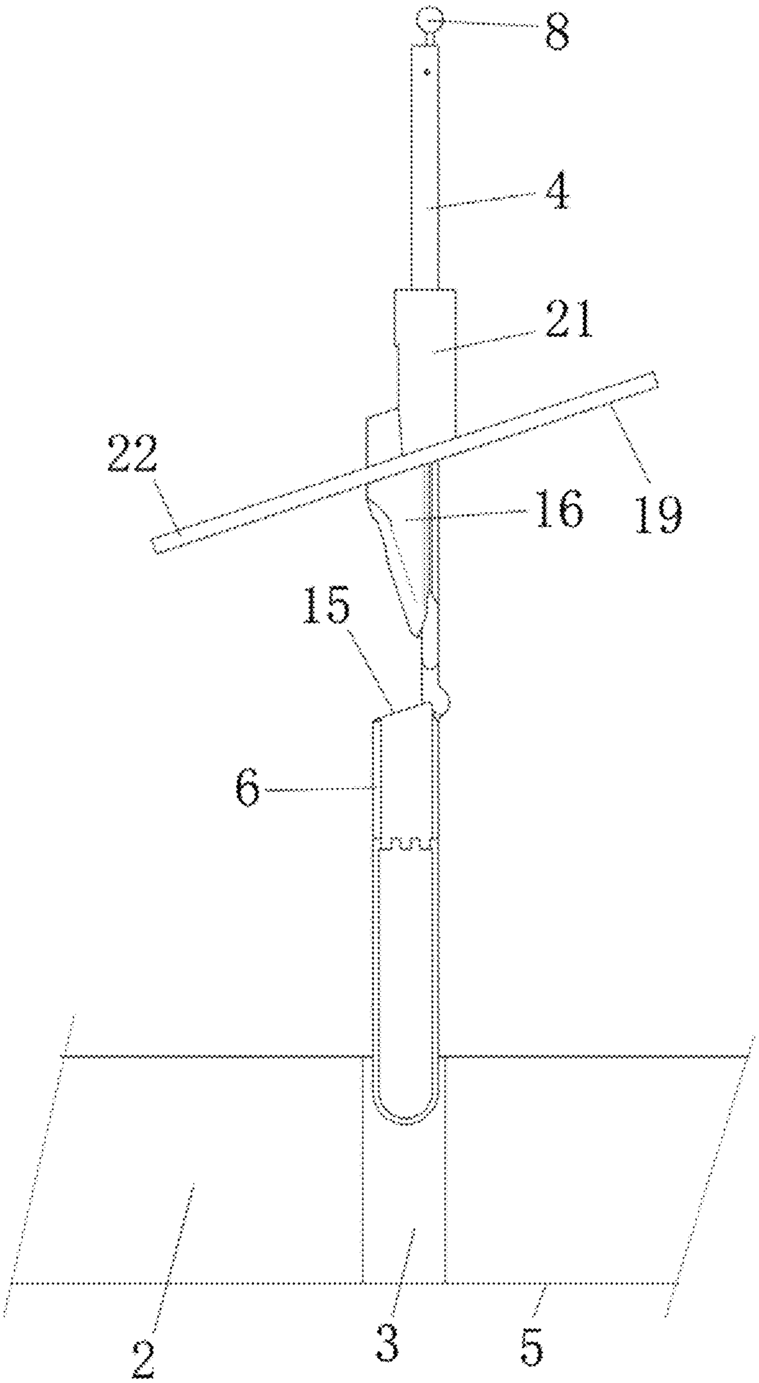
FIG. 6 is a schematic view of the tissue suturing device of FIG. 1 entering a wound to be sutured.

Additionally, referring to FIG. 6, the positioning contact surface 19 and the tube opening edge 15 of the tube segment 6 are parallel to each other, and the tube opening edge 15 is configured to contact the tissue wall 5. In this way, the positioning contact surface 19 and the tube opening edge 15 parallel to each other can clamp the cavity wall tissue more steadily.

In addition, the positioning device 18 can be of various types, and any type is possible, as long as the positioning device 18 can be movably arranged on the guide segment 4 and comprises the positioning contact surface 19. For example, referring to FIG. 1 and FIG. 5, the positioning device 18 comprises a positioning plate 20 and a sleeve 21 arranged tilted on the positioning plate 20, where the positioning plate 20 comprises the positioning contact surface, and the sleeve 21 is sleeved on the guide segment 4 and a positioning structure is arranged therebetween. For example, referring to FIG. 6 and FIG. 7, when the body 1 is arranged vertically, after the sleeve 21 is sleeved on the guide segment 4, the positioning plate 20 and the tube opening edge 15 will be obliquely arranged parallel to each other. When the tissue suturing device tilts to either side in the wound to be sutured, the positioning contact surface 19 and the tube opening edge 15 will be arranged horizontally, thereby to clamp the cavity wall tissue more steadily.

In addition, a rotary knob 26 may be arranged on a tube wall of the sleeve 21, and the rotary knob 26 has a locking bolt. By tightening the locking bolt against the guide segment 4, the sleeve 21 can be maintained positioned at a desired set position.

Figure 5:
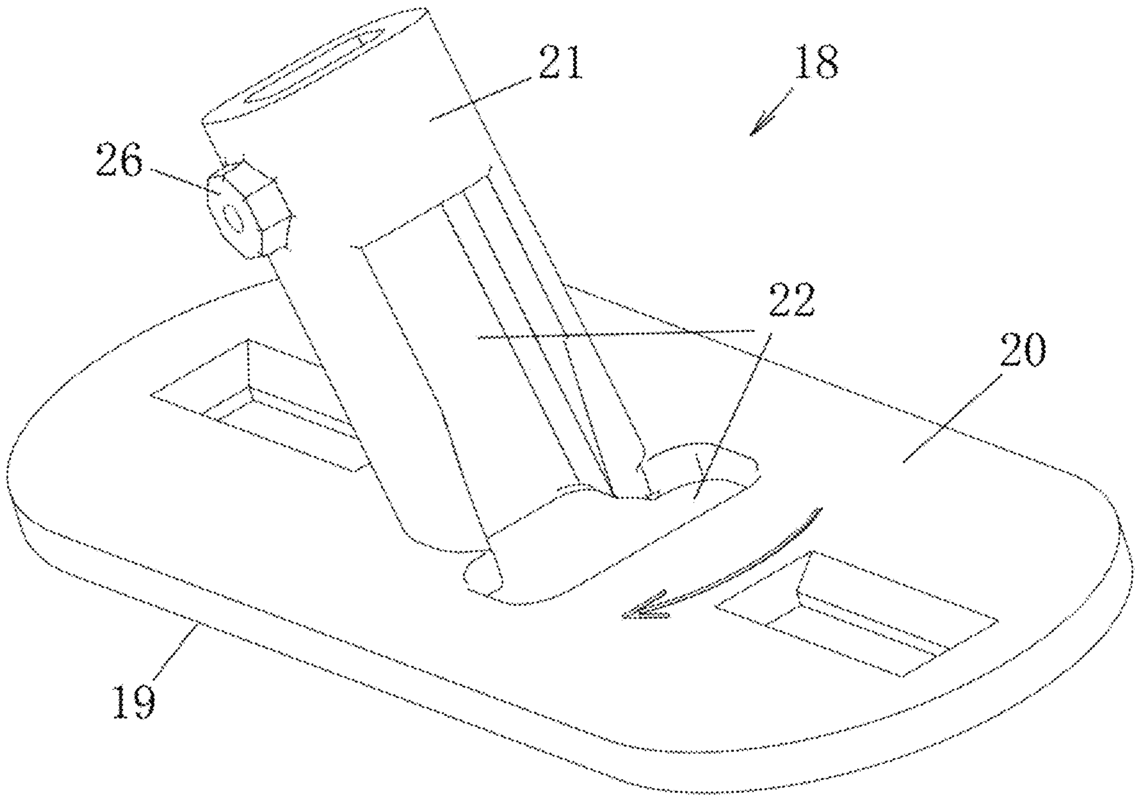
FIG. 5 is a schematic view of a three-dimensional structure of a suture thread positioning segment of the tissue suturing device of FIG. 1.

Additionally, referring to FIG. 1 and FIG. 5, an avoidance opening 22 is formed at an obtuse angle connection position between the positioning plate 20 and the sleeve 21, and the avoidance opening 22 is configured to accommodate at least a portion of the suture thread positioning segment 16 of the body 1 between the guide segment 4 and the tube segment 6. Thus, the moving range of the positioning device 18 can be expanded so that the positioning device 18 can be moved to the position of the suture thread positioning segment 16.

Figure 2:
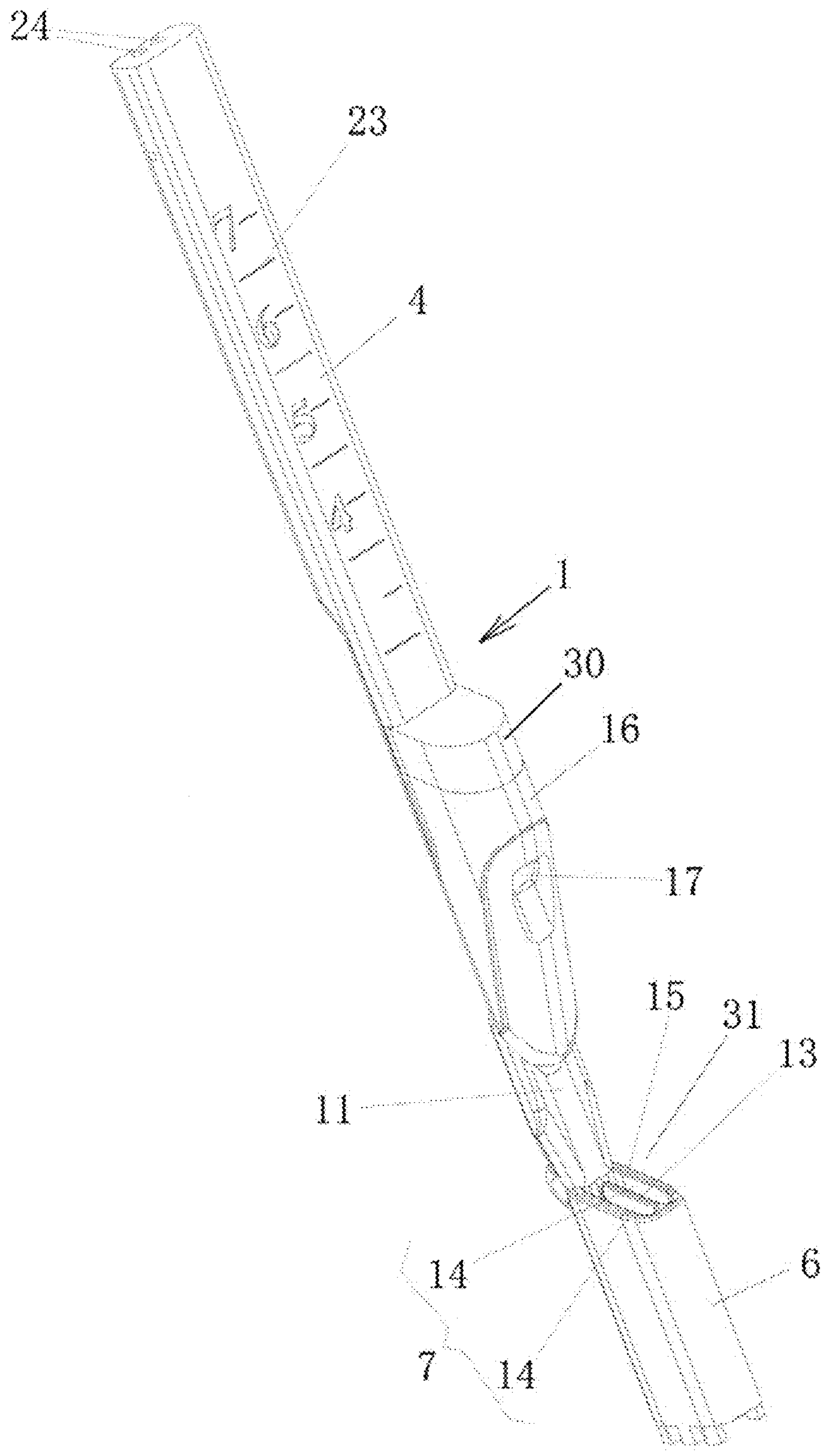
FIG. 2 is a schematic view of a three-dimensional structure of a body of another tissue suturing device provided by a specific embodiment of the invention.
Figure 3:
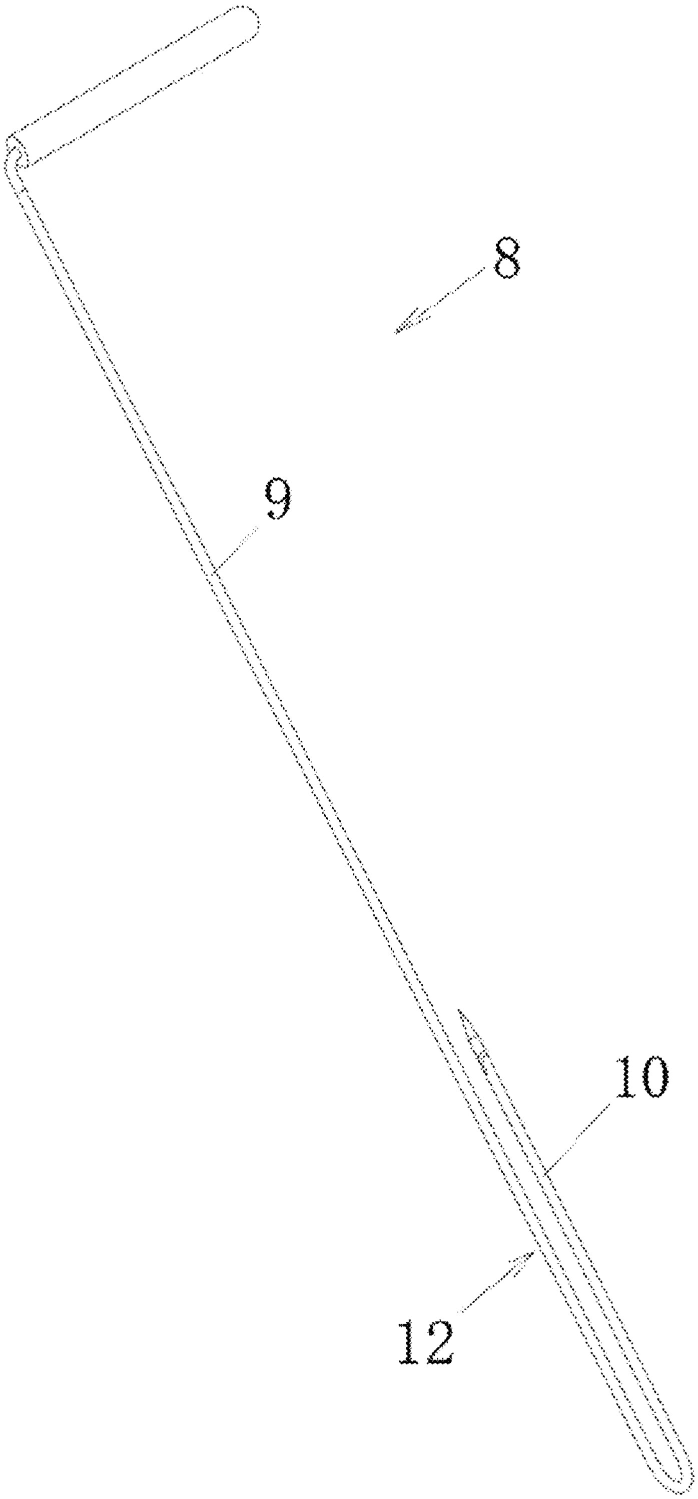
FIG. 3 is a schematic view of a three-dimensional structure of a suture needle of the tissue suturing device of FIG. 1.
Figure 4:
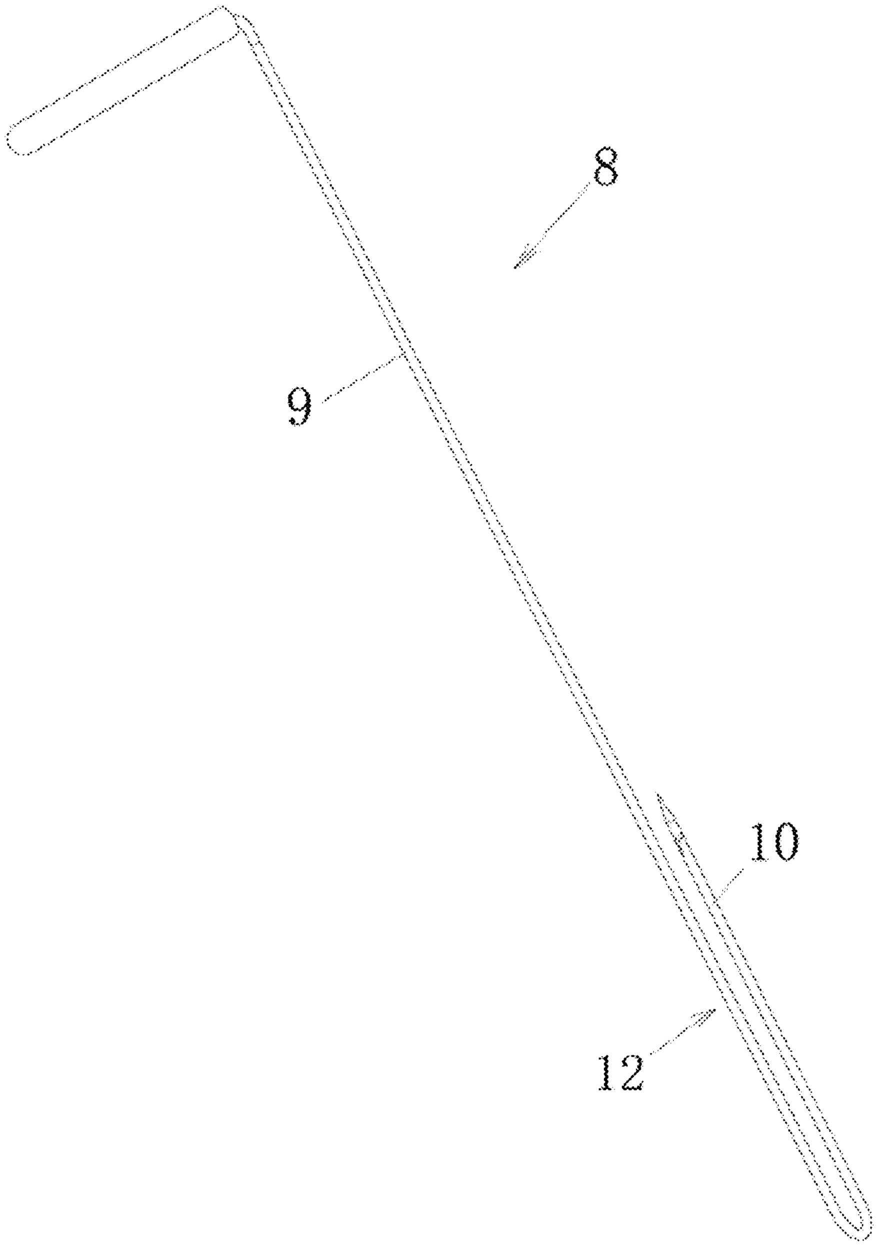
FIG. 4 is a schematic view of a three-dimensional structure of another suture needle of the tissue suturing device of FIG. 1.

Moreover, referring to FIG. 1 and FIG. 2, the guide segment 4 is provided thereon with a scale line 23 configured to mark the movement of the positioning device 18 to a predetermined position. In this way, the positioning device 18 can be moved to a desired scale position as needed, and then maintained at the position.

Moreover, the guide segment 4 is provided thereon with a plurality of locking structures that can be unlocked, each of which is configured to lock and unlock the corresponding suture needle. For example, referring to FIG. 1, the locking structure comprises a locking bolt and a radial hole 27 on the guide segment 4. When the puncture needle segment 10 is located in the accommodating cavity, the locking bolt can be threaded into the radial hole 27 and tightened against the main needle segment of the suture needle, thereby limiting the movement of the suture needle. In addition, each suture needle has its own corresponding locking structure.

Moreover, the inner tissue wall suturing device comprises a suture thread 29. The suture thread 29 can be connected between the puncture needle segments 10 of two suture needles, and the puncture needle segments 10 can carry the suture thread 29 and be located in the accommodating cavity 7. In this way, the suture thread 29 can be connected in advance between the puncture needle segments 10 and preset in the accommodating cavity 7.

Figure 8:
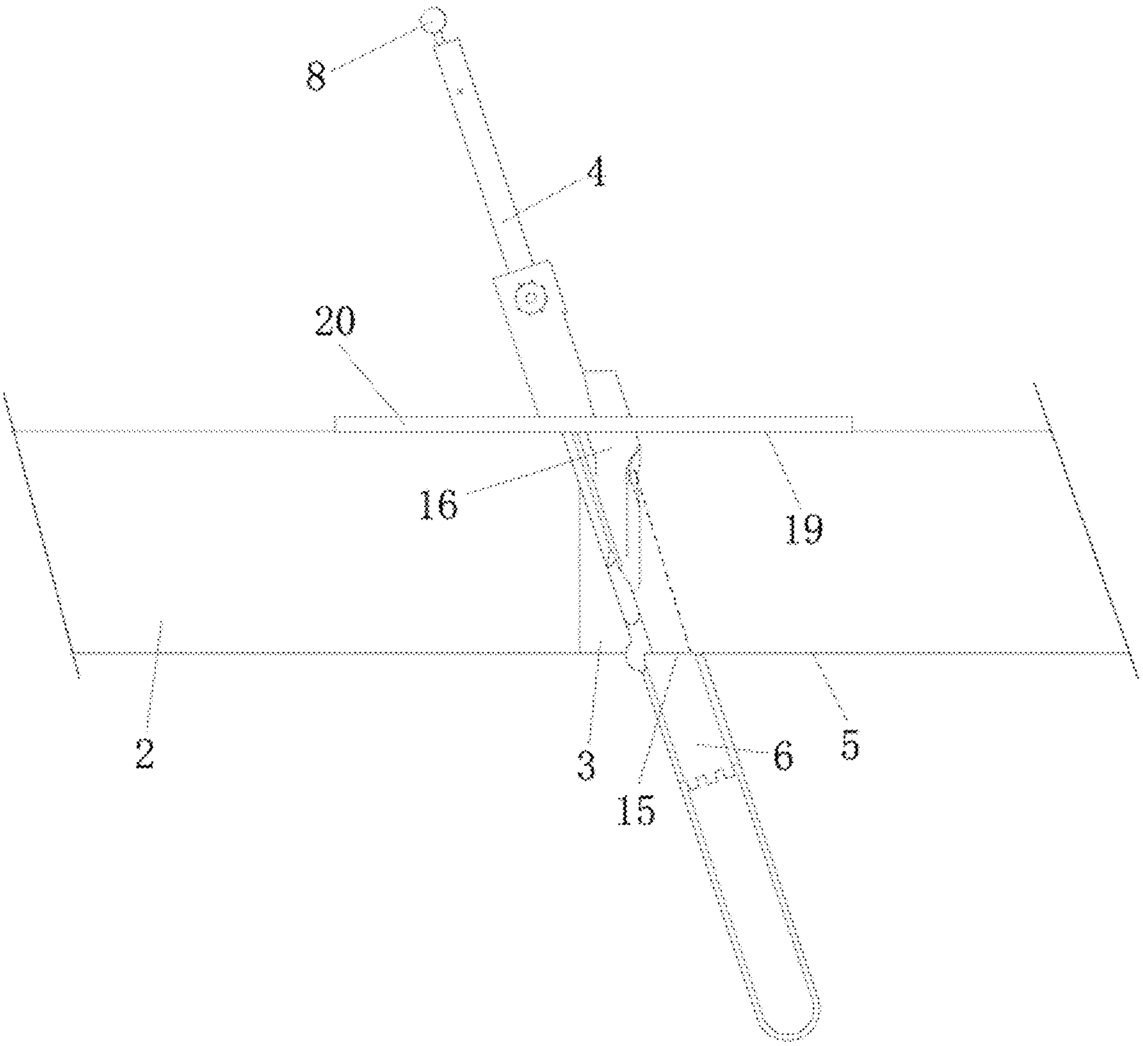
FIG. 8 is a schematic view of the tissue suturing device of FIG. 1 arranging a suture thread on the other side, such as the right side, of the wound to be sutured, after arranging a suture thread on one side, such as the left side, of the wound to be sutured, as shown in FIG. 7.
Figure 9:
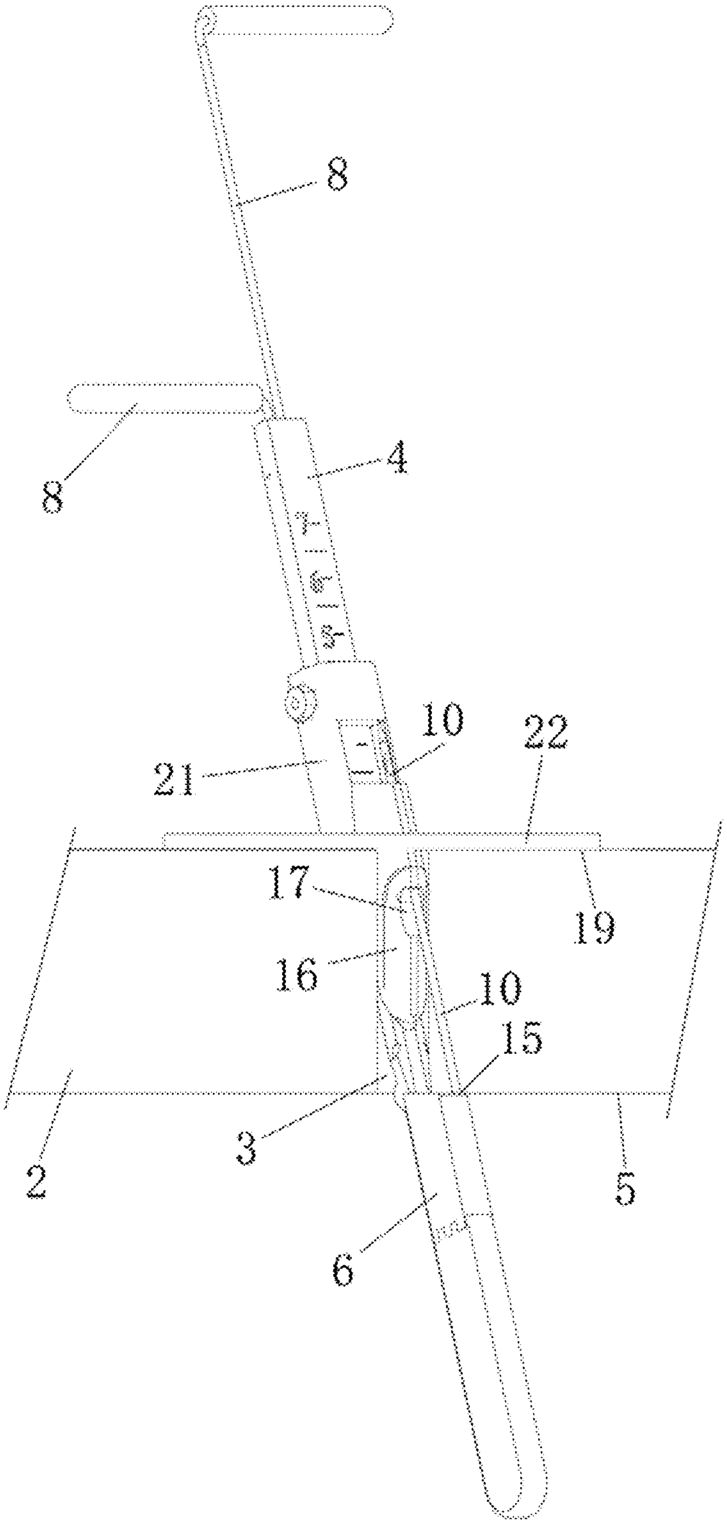
FIG. 9 is a schematic steric view of arranging the suture thread as shown in FIG. 8, showing that the puncture needle segment passes through at least part of the tissue from the inside to the outside after a suture needle is pulled outward.
Figure 10:
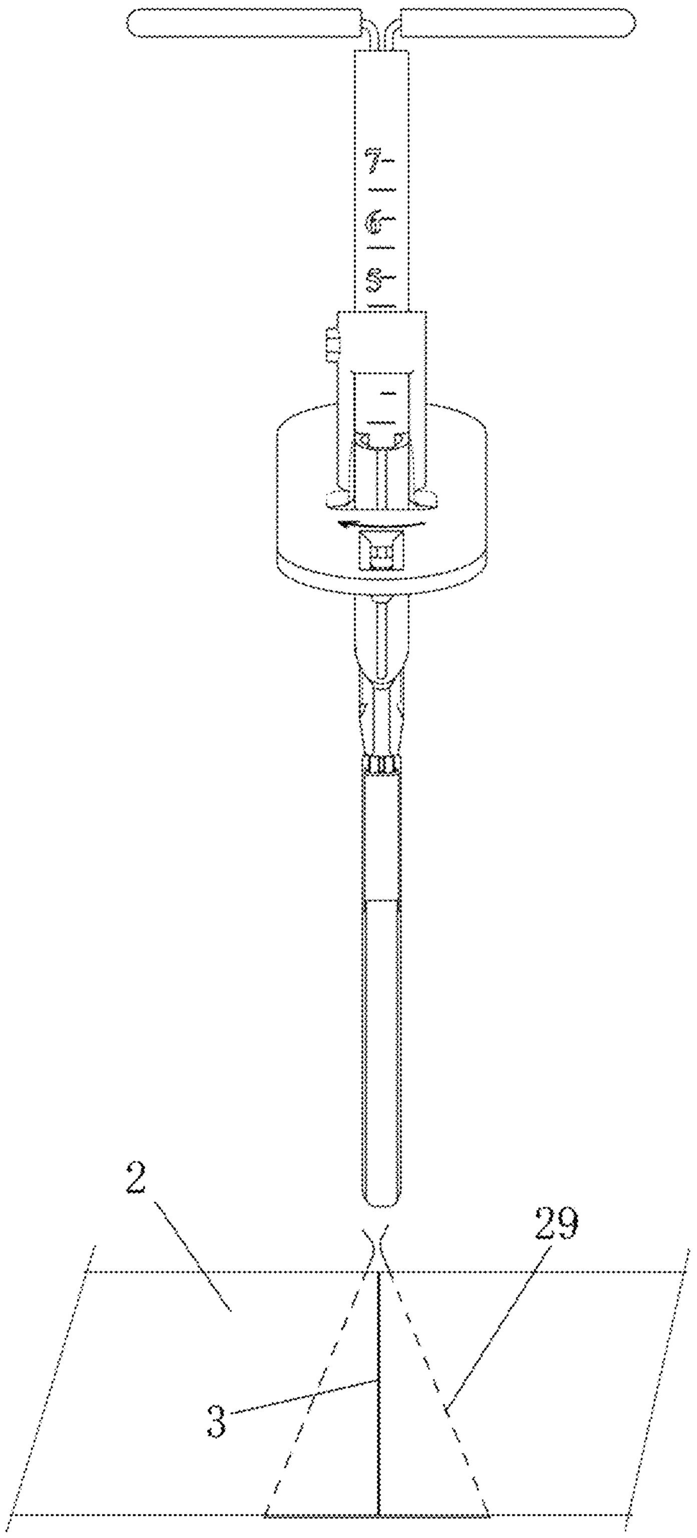
FIG. 10 is a schematic view of the tissue suturing device of FIG. 1 suturing a wound to be sutured with a suture thread after arranging the suture thread and then withdrawing.

An application process of a tissue suturing device is described below in combination with FIG. 1 and FIG. 6-FIG. 10: A suture thread can be connected between two puncture needle segments 10, and the two puncture needle segments 10 are preset with the suture thread in the accommodating cavity 7. As shown in FIG. 6, the guide segment 4 is vertically inserted into the wound to be sutured 3 such that tube segment 6 is located in the inner cavity 28. As shown in FIG. 7, the body 1 is tilted to the right, and the positioning device 18 is moved on the guide segment 4 to allow the positioning contact surface 19 and the tube opening edge 15 to contact the cavity wall tissue 2, and then one suture needle 8 is pulled outward, as shown by the dotted line in FIG. 7. The puncture needle segment 10 of the suture needle 8 is allowed to puncture with the suture thread obliquely from the inside to the outside on the left side of the wound to be sutured to draw one thread end of the suture thread into the suture thread positioning segment 16. The puncture needle segment 10 is then moved inward and returned to the accommodating cavity 6 to complete the arrangement of the suture thread on the left side. The tissue suturing device is then rotated approximately 180°, as shown in FIG. 8, to tilt to the left side, and the other suture needle 8 is pulled outward, as shown by the dotted line in FIG. 8. The puncture needle segment 10 of the suture needle 8 is allowed to puncture with the suture thread obliquely from the inside to the outside on the right side of the wound to be sutured to draw the other thread end of the suture thread into the suture thread positioning segment 16, referring to FIG. 9. Then the puncture needle segment 10 is moved inward and returned to the accommodating cavity 6 to complete the arrangement of the suture thread on the right side, and then the tissue suturing device is restored to vertical placement and taken out. The operator then sutures the wound to be sutured 3 using the arranged suture thread 29.

It should be understood by those skilled in the art that the above embodiments are all exemplary and not restrictive. Different technical features present in different embodiments can be combined to achieve beneficial effects. On the basis of studies on the attached drawings, the specification and the claims, those skilled in the art shall be able to understand and realize other variations of the disclosed embodiments. Any reference numbers in the claims shall not be construed to limit the scope of protection. The appearance of certain technical features in different dependent claims does not mean that these technical features cannot be combined to achieve beneficial effects.

The invention claimed is:

1. A tissue suturing device, comprising:

a body (1), comprising a guide segment (4) at a proximal end for extending into a wound to be sutured (3) and a tube segment (6) at a distal end, wherein the guide segment (4) is provided with a suture needle channel, and the tube segment (6) is provided therein with an accommodating cavity (7) communicated with the suture needle channel;

a plurality of suture needles (8), each of which comprising a main needle segment (9) and a puncture needle segment (10) connected with and spaced apart from the main needle segment (9), wherein two of the suture needles are used as a group of suture needles to connect a suture thread releasably between the puncture needle segments (10) of the two suture needles, the main needle segments (9) of the plurality of the suture needles (8) are configured to be arranged in the suture needle channel, and the puncture needle segments (10) are configured to carry the suture thread and be located in the accommodating cavity (7);

wherein each of the suture needles (8) is configured to move toward the proximal end and the distal end along the suture needle channel such that the puncture needle segment (10) is configured to return to the accommodating cavity (7) alone after passing with the suture thread through a tissue wall (5).

2. The tissue suturing device according to claim 1, wherein the body (1) comprises a connecting piece (11), and the guide segment (4) is connected with the tube segment (6) through the connecting piece (11) to form an avoidance space at a tube opening edge (15) of the tube segment (6).

3. The tissue suturing device according to claim 1, wherein each of the suture needles (8) comprises a U-shaped needle (12), the main needle segment (9) and the U-shaped needle (12) are connected, and at least one side needle segment of the U-shaped needle (12) is used as the puncture needle segment (10).

4. The tissue suturing device according to claim 3, wherein one side needle segment of the U-shaped needle (12) is connected with the main needle segment (9), and the other side needle segment of the U-shaped needle (12) is used as the puncture needle segment (10).

5. The tissue suturing device according to claim 1, wherein the accommodating cavity (7) is provided therein with a partition board (13), the partition board (13) divides the accommodating cavity (7) into a plurality of chambers (14), and the puncture needle segment (10) of each of the suture needles (8) is configured to be located in the respective corresponding chamber (14).

6. The tissue suturing device according to claim 5, wherein a suture thread pre-positioning slot is formed on the partition board (13).

7. The tissue suturing device according to claim 1, wherein the suture needle channel is provided therein with a partition board, the partition board divides the suture needle channel into a plurality of channel holes, and the main needle segment (9) of each of the suture needles (8) is configured to be located in the respective corresponding channel hole.

8. The tissue suturing device according to claim 1, wherein a tube opening edge (15) of the tube segment (6) is tilted and extended downward such that when the body (1) is tilted to one side in the wound to be sutured, the tube opening edge (15) tilted and extended downward is configured to be horizontally arranged to contact the tissue wall on the other side of the wound to be sutured.

9. The tissue suturing device according to claim 1, wherein the body (1) comprises a suture thread positioning segment (16) between the guide segment (4) and the tube segment (6), and the suture thread positioning segment (16) is configured to allow the puncture needle segment (10) to puncture with the suture thread, and allow the suture thread to detach from the puncture needle segment (10) and remain positioned on the suture thread positioning segment (16) when the puncture needle segment (10) withdraws.

10. The tissue suturing device according to claim 9, wherein the suture thread positioning segment (16) is provided with an elastomer, and the elastomer is configured to expand when the puncture needle segment (10) passes through with the suture thread, and shrink when the puncture needle segment (10) withdraws to allow the suture thread to detach from the puncture needle segment (10) and remain positioned on the elastomer.

11. The tissue suturing device according to claim 10, wherein the suture thread positioning segment (16) comprises a housing channel (17) in which the elastomer is arranged.

12. The tissue suturing device according to claim 9, wherein the suture thread positioning segment (16) is provided with a suture needle passing channel, and the main needle segments (9) of the plurality of suture needles (8) are configured to be movably arranged in the suture needle passing channel.

13. The tissue suturing device according to claim 12, wherein the suture thread positioning segment (16) is formed into a cone, a large-diameter end of the cone is oriented toward the guide segment (4), a small-diameter end of the cone is oriented toward the tube segment (6), and an inner channel of the cone is used as the suture needle passing channel.

14. The tissue suturing device according to claim 1, wherein the tissue suturing device comprises a positioning device (18) which is arranged on the guide segment (4) and is configured to be moved along the guide segment to a set position, wherein the positioning device (18) comprises a positioning contact surface (19) configured to contact an outer surface of a cavity wall tissue to clamp the cavity wall tissue together with the tube segment (6).

15. The tissue suturing device according to claim 14, wherein the positioning contact surface (19) and a tube opening edge (15) of the tube segment (6) are parallel to each other, and the tube opening edge (15) is configured to contact the tissue wall (5).

16. The tissue suturing device according to claim 14, wherein the positioning device (18) comprises a positioning plate (20) and a sleeve (21) arranged tilted on the positioning plate (20), the positioning plate (20) comprises the positioning contact surface, and the sleeve (21) is sleeved on the guide segment (4) and a tightener is arranged therebetween.

17. The tissue suturing device according to claim 16, wherein an avoidance opening (22) is formed at an obtuse angle connection position between the positioning plate (20) and the sleeve (21), and the avoidance opening (22) is configured to accommodate at least a portion of a suture thread positioning segment (16) of the body (1) between the guide segment (4) and the tube segment (6).

18. The tissue suturing device according to claim 14, wherein the guide segment (4) is provided thereon with a scale line (23) configured to mark the movement of the positioning device (18) to a predetermined position.

19. The tissue suturing device according to claim 1, wherein the guide segment (4) is provided thereon with a plurality of locking structures that are configured to be unlocked, each of which is configured to lock and unlock the corresponding suture needle.

20. The tissue suturing device according to claim 1, wherein the tissue suturing device comprises a suture thread, the suture thread is connected between the puncture needle segments (10) of two of the suture needles, and the puncture needle segments (10) are configured to carry the suture thread and be located in the accommodating cavity (7).

* * * * *